(12) United States Patent
Evenson et al.

(10) Patent No.: US 9,675,499 B2
(45) Date of Patent: Jun. 13, 2017

(54) CONTAINMENT PANT WITH ATTACHMENT MECHANISMS

(71) Applicant: Kimberly-Clark Worldwide, Inc., Neenah, WI (US)

(72) Inventors: Stacy Elaine Evenson, Neenah, WI (US); Brooke Berg, Neenah, WI (US); Lewis Orchard, Neenah, WI (US); Patricia Ann Abney, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 14/782,808

(22) PCT Filed: Nov. 25, 2014

(86) PCT No.: PCT/US2014/067249
§ 371 (c)(1),
(2) Date: Oct. 7, 2015

(87) PCT Pub. No.: WO2016/085462
PCT Pub. Date: Jun. 2, 2016

(65) Prior Publication Data
US 2016/0317364 A1    Nov. 3, 2016

(51) Int. Cl.
*A61F 13/15* (2006.01)
*A61F 13/496* (2006.01)
(Continued)

(52) U.S. Cl.
CPC ...... *A61F 13/496* (2013.01); *A61F 13/49011* (2013.01); *A61F 13/49019* (2013.01);
(Continued)

(58) Field of Classification Search
CPC .......... A61F 13/15268; A61F 13/49006; A61F 13/49019; A61F 13/49413; A61F 13/496;
(Continued)

(56) References Cited

U.S. PATENT DOCUMENTS 1,959,282 A  5/1934 Bade
2,840,078 A  6/1958 Smith
(Continued)

FOREIGN PATENT DOCUMENTS

CN  201790964 U  4/2011
EP  0 274 753 A2  7/1988
(Continued)

OTHER PUBLICATIONS

Co-pending U.S. Appl. No. 29/459,644, filed Jul. 2, 2013, by De Bruin et al. for "Portion of an Absorbent Article."
(Continued)

*Primary Examiner* — Lynne Anderson

(57) ABSTRACT

A permanently closed containment pant including a chassis and a sling that is positioned within the chassis and is joined to the front waist region and the back waist region is disclosed. The sling is attached to the chassis with an attachment mechanism to secure the sling to the chassis. The attachment mechanism may comprise a bonded attachment and an attachment elastic material at a middle portion of the sling to the chassis at the crotch region; a bond attachment adjacent the pouch in a transition material; or elastics extending from the leg openings and attaching to the sling in the crotch region.

16 Claims, 11 Drawing Sheets

(51) Int. Cl.
*A61F 13/505* (2006.01)
*A61F 13/70* (2006.01)
*A61F 13/49* (2006.01)
*A61F 13/74* (2006.01)

(52) U.S. Cl.
CPC ........ *A61F 13/4963* (2013.01); *A61F 13/505* (2013.01); *A61F 13/70* (2013.01); *A61F 13/74* (2013.01); *A61F 2013/49092* (2013.01)

(58) Field of Classification Search
CPC ........ A61F 13/505; A61F 13/66; A61F 13/74; A61F 2013/15276; A61F 2013/49092; A61F 2013/5055
See application file for complete search history.

(56) References Cited

U.S. PATENT DOCUMENTS

| | | |
|---|---|---|
| 2,881,761 A | 4/1959 | Kenner |
| 2,985,170 A | 5/1961 | Title |
| 3,000,381 A | 9/1961 | Mulhole et al. |
| 3,079,922 A | 3/1963 | Papajohn |
| 3,874,385 A | 4/1975 | Gellert |
| 3,916,900 A | 11/1975 | Breyer et al. |
| 4,034,760 A | 7/1977 | Amirsakis |
| 4,381,781 A | 5/1983 | Sciaraffa et al. |
| 4,568,342 A | 2/1986 | Davis |
| 4,604,096 A | 8/1986 | Dean et al. |
| 4,605,404 A | 8/1986 | Sneider |
| 4,642,110 A | 2/1987 | Dudek |
| 4,695,279 A | 9/1987 | Steer |
| 4,735,624 A | 4/1988 | Mazars |
| 4,762,521 A | 8/1988 | Roessler et al. |
| 4,772,282 A | 9/1988 | Oakley |
| 4,834,737 A | 5/1989 | Khan |
| 4,865,597 A | 9/1989 | Mason, Jr. et al. |
| 4,865,916 A | 9/1989 | Yamaura et al. |
| 4,955,880 A | 9/1990 | Rodriquez |
| 4,964,857 A | 10/1990 | Osborn |
| 5,032,119 A | 7/1991 | Hookano |
| 5,069,672 A | 12/1991 | Wippler et al. |
| 5,098,423 A | 3/1992 | Pieniak et al. |
| 5,108,385 A | 4/1992 | Snyder |
| D327,319 S | 6/1992 | Ruffo et al. |
| 5,207,663 A | 5/1993 | McQueen |
| 5,210,882 A | 5/1993 | Moretz et al. |
| 5,217,447 A | 6/1993 | Gagnon |
| 5,217,782 A | 6/1993 | Moretz et al. |
| 5,221,277 A | 6/1993 | Beplate |
| 5,236,428 A | 8/1993 | Zajaczkowski |
| D343,681 S | 1/1994 | Hull |
| 5,290,269 A | 3/1994 | Heiman |
| 5,290,270 A | 3/1994 | Fisher |
| 5,291,617 A | 3/1994 | Moretz et al. |
| 5,306,536 A | 4/1994 | Moretz et al. |
| 5,315,717 A | 5/1994 | Moretz et al. |
| H1340 H | 7/1994 | Yetter et al. |
| 5,325,543 A | 7/1994 | Allen |
| 5,360,422 A | 11/1994 | Brownlee et al. |
| 5,387,208 A | 2/1995 | Ashton et al. |
| 5,397,318 A | 3/1995 | Dreier |
| 5,405,342 A | 4/1995 | Roessler et al. |
| 5,409,476 A | 4/1995 | Coates |
| 5,458,591 A | 10/1995 | Roessler et al. |
| 5,514,104 A | 5/1996 | Cole et al. |
| 5,558,661 A | 9/1996 | Roe et al. |
| 5,562,648 A | 10/1996 | Peterson |
| 5,643,242 A | 7/1997 | Lavon et al. |
| 5,669,902 A | 9/1997 | Sivilich |
| 5,707,364 A | 1/1998 | Coates |
| 5,795,348 A | 8/1998 | Roe et al. |
| 5,814,037 A | 9/1998 | Coates |
| 5,830,201 A | 11/1998 | George et al. |
| 5,891,120 A | 4/1999 | Chmielewski |
| 5,891,122 A | 4/1999 | Coates |
| 6,007,528 A | 12/1999 | Osborn, III |
| D421,802 S | 3/2000 | Roessler et al. |
| D422,077 S | 3/2000 | Suprise et al. |
| 6,061,839 A | 5/2000 | Smolik |
| D436,400 S | 1/2001 | Kiecker |
| 6,168,585 B1 | 1/2001 | Cesco-Cancian |
| 6,183,458 B1 | 2/2001 | Ahlstrand et al. |
| D438,614 S | 3/2001 | Ratliff et al. |
| D438,615 S | 3/2001 | Dimitrijevs et al. |
| D439,662 S | 3/2001 | Ratliff et al. |
| 6,229,061 B1 | 5/2001 | Dragoo et al. |
| 6,254,583 B1 | 7/2001 | Coates |
| 6,262,331 B1 | 7/2001 | Nakahata et al. |
| D452,315 S | 12/2001 | Coates |
| 6,359,192 B1 | 3/2002 | Schmidt et al. |
| D456,508 S | 4/2002 | Schroeder et al. |
| D457,950 S | 5/2002 | Schroeder et al. |
| D457,951 S | 5/2002 | Abney et al. |
| D462,439 S | 9/2002 | Montgomery et al. |
| D463,022 S | 9/2002 | Montgomery et al. |
| D463,858 S | 10/2002 | Sherrod et al. |
| 6,468,257 B1 | 10/2002 | Ono et al. |
| 6,486,379 B1 | 11/2002 | Chen et al. |
| D470,935 S | 2/2003 | Sherrod et al. |
| 6,575,952 B2 | 6/2003 | Kirk et al. |
| 6,605,071 B1 | 8/2003 | Gray et al. |
| 6,623,466 B1 | 9/2003 | Richardson |
| 6,786,895 B1 | 9/2004 | Schmitz |
| 6,807,685 B1 * | 10/2004 | Hasegawa ............... A41B 9/004 2/400 |
| 6,808,516 B2 | 10/2004 | Tsuji et al. |
| 6,848,121 B1 | 2/2005 | Halid |
| 6,890,325 B2 | 5/2005 | Edens et al. |
| 6,895,603 B2 | 5/2005 | Coates |
| 6,926,705 B1 | 8/2005 | Coates |
| 7,052,485 B2 | 5/2006 | Suzuki |
| 7,156,832 B2 | 1/2007 | Drevik et al. |
| 7,166,095 B1 | 1/2007 | Coates |
| 7,175,613 B2 | 2/2007 | Sugiyama et al. |
| 7,264,615 B2 | 9/2007 | Sherrod et al. |
| 7,322,966 B1 | 1/2008 | Deerin |
| D561,334 S | 2/2008 | Martynus et al. |
| 7,387,620 B2 | 6/2008 | Watanabe et al. |
| 7,393,346 B2 | 7/2008 | Morman et al. |
| 7,410,479 B2 * | 8/2008 | Hoshino ........... A61F 13/49019 604/385.24 |
| D595,844 S | 7/2009 | Giloh |
| D609,805 S | 2/2010 | Moravek et al. |
| 7,749,210 B2 | 7/2010 | Mishima et al. |
| 7,824,387 B2 | 11/2010 | Lavon |
| D636,487 S | 4/2011 | Nnenna |
| 7,938,814 B2 | 5/2011 | Koyama et al. |
| 7,959,618 B2 | 6/2011 | Hermansson et al. |
| D643,919 S | 8/2011 | Walker et al. |
| 8,216,201 B2 | 7/2012 | Beck |
| D679,004 S | 3/2013 | Norman et al. |
| 2002/0016579 A1 | 2/2002 | Stenberg |
| 2002/0032422 A1 | 3/2002 | Goyarts |
| 2002/0133134 A1 | 9/2002 | Wilbon |
| 2002/0143309 A1 | 10/2002 | Glasgow et al. |
| 2002/0165515 A1 | 11/2002 | Burnham |
| 2002/0169479 A1 | 11/2002 | Vesnaver |
| 2002/0177829 A1 | 11/2002 | Fell et al. |
| 2003/0004484 A1 | 1/2003 | Hammons et al. |
| 2003/0163105 A1 | 8/2003 | Tears et al. |
| 2003/0181883 A1 | 9/2003 | Olson et al. |
| 2003/0199844 A1 | 10/2003 | Lavon et al. |
| 2003/0216705 A1 | 11/2003 | Coates |
| 2004/0102751 A1 | 5/2004 | Schueler |
| 2004/0127867 A1 | 7/2004 | Odorzynski et al. |
| 2005/0124957 A1 | 6/2005 | Giloh |
| 2005/0210560 A1 | 9/2005 | Coates |
| 2005/0256487 A1 | 11/2005 | Williams |
| 2006/0167432 A1 | 7/2006 | Sigari |
| 2006/0206085 A1 | 9/2006 | Gegelys et al. |
| 2006/0247599 A1 | 11/2006 | Mullen et al. |
| 2007/0135788 A1 | 6/2007 | Damay et al. |
| 2008/0065039 A1 | 3/2008 | Labit et al. |
| 2008/0082071 A1 | 4/2008 | Bryant et al. |

(56) References Cited

U.S. PATENT DOCUMENTS

| | | |
|---|---|---|
| 2008/0110775 A1 | 5/2008 | Beck et al. |
| 2008/0215028 A1 | 9/2008 | Brown et al. |
| 2008/0312632 A1 | 12/2008 | Fernfors |
| 2009/0264851 A1 | 10/2009 | Richlen et al. |
| 2009/0299313 A1 | 12/2009 | Knightingale et al. |
| 2010/0114048 A1 | 5/2010 | Bishop et al. |
| 2010/0130955 A1 | 5/2010 | Tice |
| 2010/0179495 A1 | 7/2010 | Roe |
| 2010/0179496 A1 | 7/2010 | Roe et al. |
| 2010/0179498 A1 | 7/2010 | Roe |
| 2010/0179499 A1 | 7/2010 | Roe |
| 2010/0179500 A1 | 7/2010 | Roe et al. |
| 2010/0179501 A1 | 7/2010 | Roe et al. |
| 2010/0179502 A1 | 7/2010 | Roe |
| 2010/0179503 A1 | 7/2010 | Roe et al. |
| 2010/0199496 A1 | 8/2010 | Demania et al. |
| 2010/0298801 A1 | 11/2010 | Beck |
| 2011/0004179 A1 | 1/2011 | Kurihara |
| 2011/0172622 A1 | 7/2011 | Roe et al. |
| 2011/0178492 A1 | 7/2011 | Coates |
| 2011/0184371 A1 | 7/2011 | Sakaguchi |
| 2011/0270211 A1 | 11/2011 | Roe et al. |
| 2011/0288515 A1 | 11/2011 | Roe et al. |
| 2011/0288518 A1 | 11/2011 | Roe et al. |
| 2012/0022492 A1 | 1/2012 | Roe |
| 2012/0029459 A1 | 2/2012 | Hallouin |
| 2012/0123364 A1 | 5/2012 | Coates |
| 2012/0123366 A1 | 5/2012 | Brownlee |
| 2012/0283680 A1 | 11/2012 | Zander et al. |
| 2014/0013490 A1 | 1/2014 | Evenson et al. |
| 2014/0018756 A1 | 1/2014 | De Bruin et al. |
| 2014/0018757 A1 | 1/2014 | De Bruin et al. |
| 2014/0018760 A1 | 1/2014 | Orchard, IV et al. |
| 2014/0018761 A1 | 1/2014 | Orchard, IV et al. |
| 2014/0018762 A1 | 1/2014 | Vignali et al. |
| 2014/0018763 A1 | 1/2014 | Evenson et al. |
| 2014/0018764 A1 | 1/2014 | Johnston et al. |
| 2015/0007382 A1 | 1/2015 | Akerley |

FOREIGN PATENT DOCUMENTS

| | | |
|---|---|---|
| EP | 0 945 110 A2 | 9/1999 |
| EP | 0 830 122 B1 | 11/2000 |
| EP | 1 117 361 B1 | 10/2004 |
| EP | 2 198 818 A1 | 6/2010 |
| EP | 1 448 140 B1 | 3/2011 |
| FR | 2 975 587 A1 | 11/2012 |
| GB | 0 140 202 A | 3/1920 |
| GB | 0 400 156 A | 10/1933 |
| GB | 0 409 056 A | 4/1934 |
| GB | 1 094 143 A | 12/1967 |
| JP | 11-033055 A | 2/1999 |
| WO | WO 95/10992 A1 | 4/1995 |
| WO | WO 96/10976 A1 | 4/1996 |
| WO | WO 98/37840 A1 | 9/1998 |
| WO | WO 98/43574 A1 | 10/1998 |
| WO | WO 02/067833 A1 | 9/2002 |
| WO | WO 2004/069093 A2 | 8/2004 |
| WO | WO 2005/122985 A1 | 12/2005 |
| WO | WO 2006/093443 A1 | 9/2006 |
| WO | WO 2007/021734 A2 | 2/2007 |
| WO | WO 2010/083290 A1 | 7/2010 |
| WO | WO 2012/009357 A1 | 1/2012 |
| WO | WO 2012/123031 A1 | 9/2012 |
| WO | WO 2013/023035 A1 | 2/2013 |

OTHER PUBLICATIONS

Co-pending U.S. Appl. No. 29/459,639, filed Jul. 2, 2013, by Evenson et al. for "Portion of a Sling for Use in a Containment Pant."

Jamilynn84, "Goodnights true fit real underwear 60-100 lbs," personal posting on Internet web page "http://www.diaperswappers.com/forum/showthread.php?t=1437993", Aug. 30, 2012, 2 pages.

* cited by examiner

CONTAINMENT PANT WITH ATTACHMENT MECHANISMS

BACKGROUND

While disposable absorbent garments offer a convenient way to manage bedwetting, many enuretic families are not satisfied with these products because they are viewed as "diaper-like" by the user who wants to wear conventional underwear. As such, many improvements have been made to disposable absorbent garments to make them more underwear-like. For example, gender specific graphics have been added and softer nonwoven materials have been utilized. However, many potential users still seek a product that looks and feels more like conventional underwear, but is still able to help manage bedwetting. Thus, there remains a need for a pant that is underwear-like yet helps to contain urine insults.

SUMMARY

In one aspect, the present invention provides a permanently closed containment pant. The chassis defines a waist opening, a first leg opening, and a second leg opening. The waist opening includes a front waist region joined with a back waist region. The containment pant also includes a sling that is positioned within the chassis and is joined to the front waist region and the back waist region. The sling includes a fluid-impervious base sheet and a containment flap joined with the base sheet to create a fluid-impervious pouch. In some embodiments of this aspect, the sling may further include a first transition and a second transition that are elastically extensible in a longitudinal direction and in a transverse direction. The second transition is a discrete piece of material joined between the pouch and the waist elastic in the back waist region. The sling is attached to the chassis in a crotch region with an attachment mechanism to secure the sling to the chassis. The attachment mechanism comprises an attachment elastic material and a bonded attachment at a middle portion of the sling to the chassis at the crotch region.

In one aspect, the present invention provides a permanently closed containment pant. The chassis defines a waist opening, a first leg opening, and a second leg opening. The waist opening includes a front waist region joined with a back waist region. The containment pant also includes a sling that is positioned within the chassis and is joined to the front waist region and the back waist region. The sling includes a fluid-impervious base sheet and a containment flap joined with the base sheet to create a fluid-impervious pouch. In some embodiments of this aspect, the sling may further include a first transition and a second transition that are elastically extensible in a longitudinal direction and in a transverse direction. The second transition is a discrete piece of material joined between the pouch and the waist elastic in the back waist region. The sling is attached to the chassis in a crotch region with an attachment mechanism to secure the sling to the chassis. The attachment mechanism comprises the attachment mechanism comprising the pair of leg elastics extending from leg openings and attaching to the sling in a crotch region.

In one aspect, the present invention provides a permanently closed containment pant. The chassis defines a waist opening, a first leg opening, and a second leg opening. The waist opening includes a front waist region joined with a back waist region. The containment pant also includes a sling that is positioned within the chassis and is joined to the front waist region and the back waist region. The sling includes a fluid-impervious base sheet and a containment flap joined with the base sheet to create a fluid-impervious pouch. In some embodiments of this aspect, the sling may further include a first transition and a second transition that are elastically extensible in a longitudinal direction and in a transverse direction. The second transition is a discrete piece of material joined between the pouch and the waist elastic in the back waist region. The sling is attached to the chassis in a crotch region with an attachment mechanism to secure the sling to the chassis, the attachment mechanism comprising a bonded attachment at a middle portion of the sling to the chassis at the crotch region, the attachment mechanism further comprising an attachment elastic material overlaying the bonded attachment.

DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

DETAILED DESCRIPTION

The containment pant of the present invention provides a durable outer chassis and an inner pouch for containing a disposable absorbent insert that is securely attached via an attachment means. In some embodiments, the containment pant is provided in a permanently closed condition. As used herein, the term "permanently closed" refers to a pant that is provided in a condition that is adapted to be only pulled on or pulled off like conventional underwear and is distinguished from pants that have refastenable fasteners and diapers that are provided in an open condition and include fasteners for securing the diapers around the body of the wearer. Suitable containment pants are also described in U.S. patent application Ser. No. 13/547,974, entitled "Containment Pant", filed on Jul. 12, 2012, the entirety of which is incorporated herein by reference.

Figure 1:
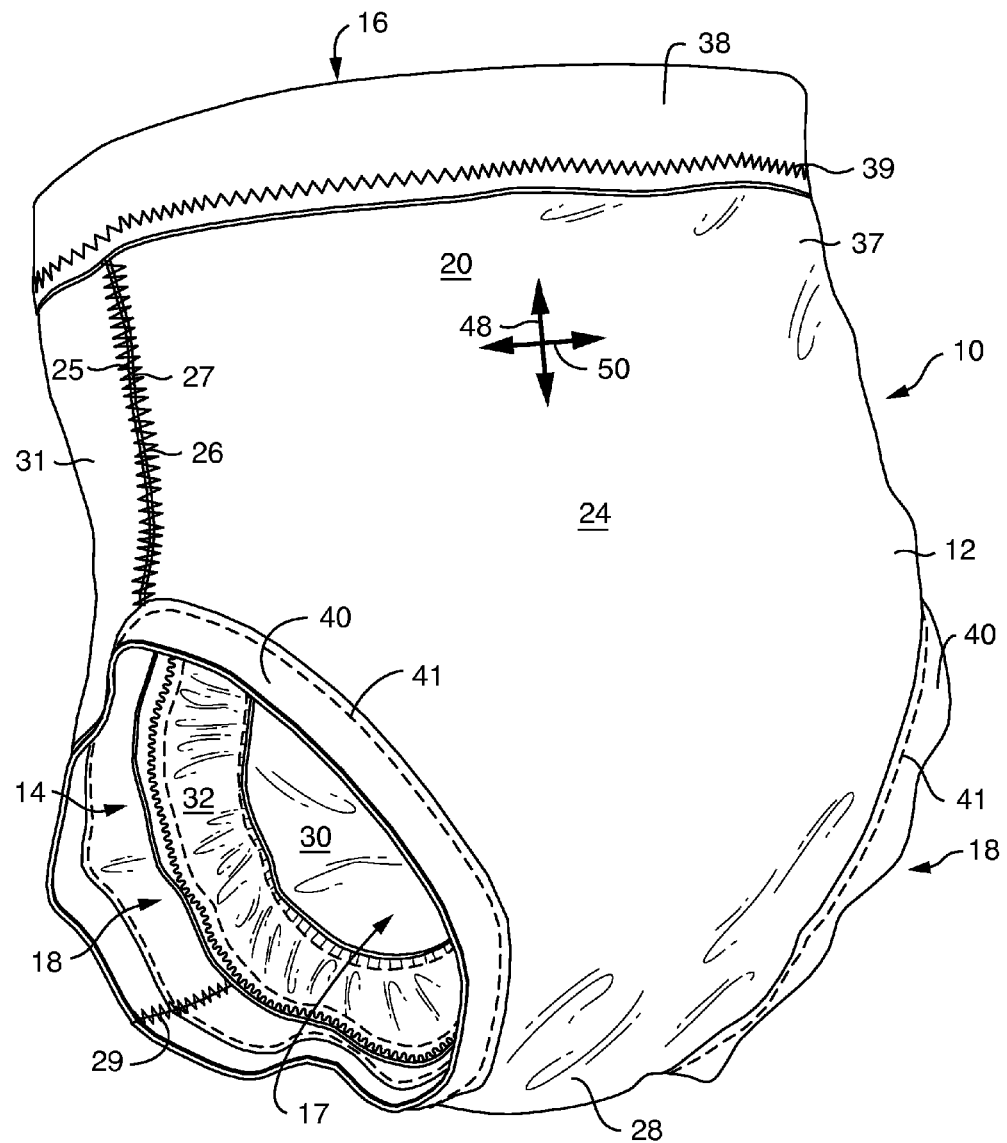
FIG. 1 representatively illustrates a front perspective view of an exemplary containment pant of the present invention.
Figure 2:
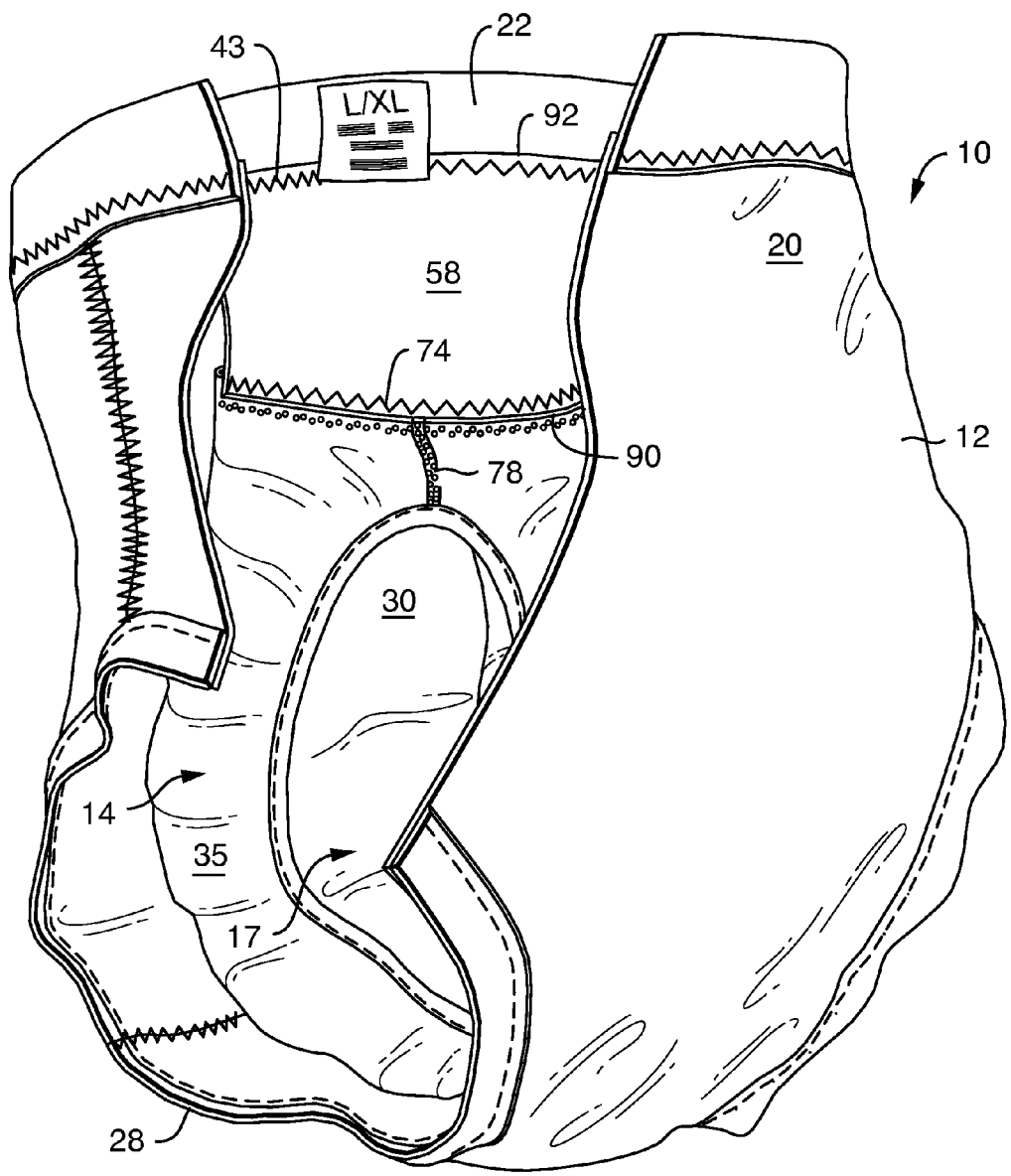
FIGS. 2 and 3 representatively illustrate side perspective views of the fully exemplary containment pant that is partially severed to illustrate internal structure.
Figure 3:
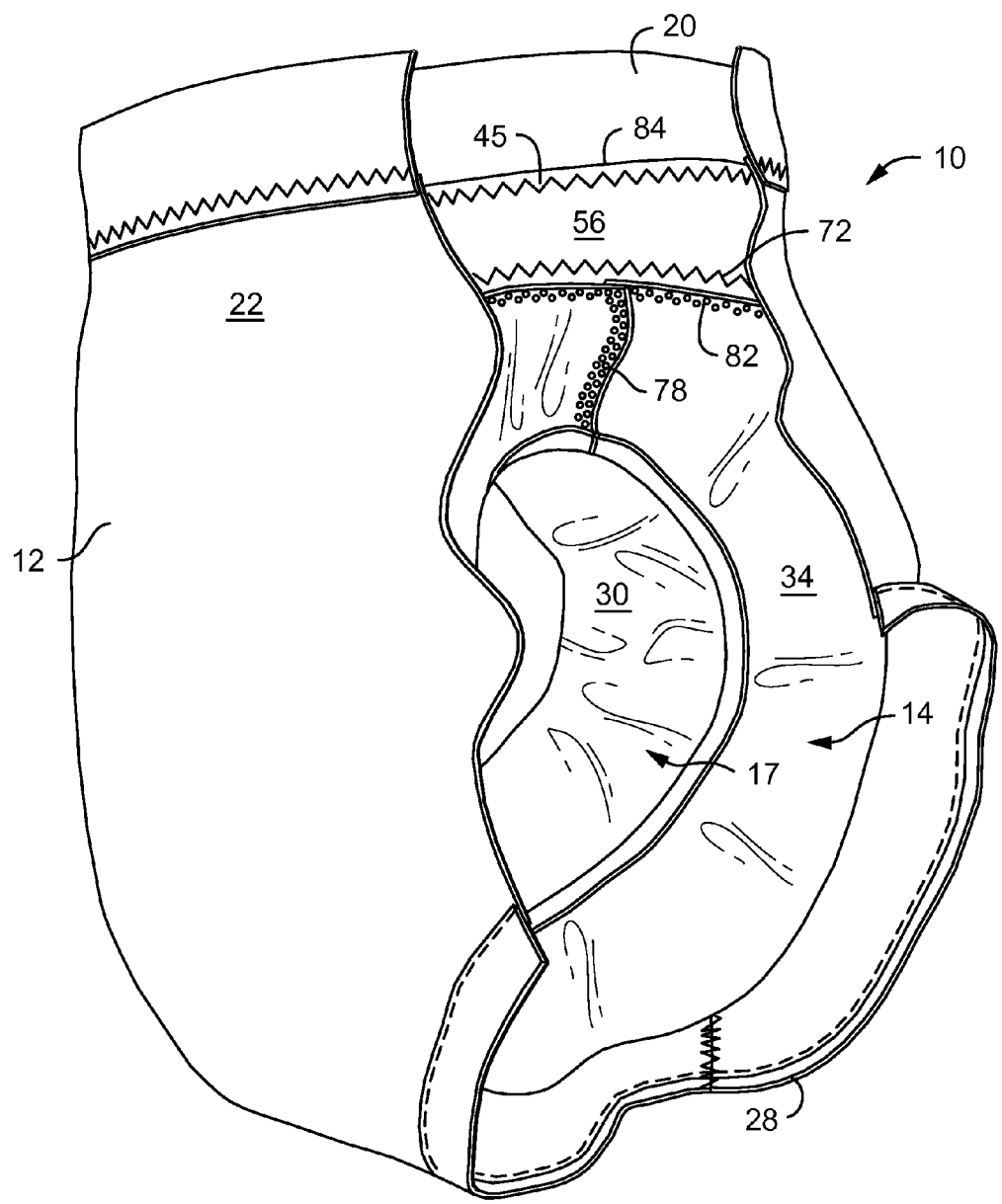

An exemplary containment pant of the present invention is representatively illustrated in FIGS. 1-3. Specifically, FIG. 1 shows a side perspective view of a containment pant 10 having a chassis 12 and a sling 14 attached within the chassis 12. The chassis 12 defines a waist opening 16 and a pair of leg openings 18. The chassis 12 also defines a front waist region 20, a back waist region 22, and a crotch region 28. The crotch region 28 is located between the front waist region 20 and the back waist region 22. The containment pant 10 of FIG. 1 is depicted in FIGS. 2 and 3 with the chassis 12 partially severed to better illustrate internal elements. FIG. 2 representatively illustrates a side perspective view with the chassis 12 partially severed to better illustrate the positioning and construction of the sling 14 in the back of the containment pant 10. FIG. 3 representatively illustrates a side perspective view with the chassis 12 partially severed to better illustrate the construction and positioning of the sling 14 in the front of the containment pant 10. The containment pant 10 defines a longitudinal direction 48 and a transverse direction 50 as illustrated in FIG. 1. The longitudinal direction 48 extends from the front waist region 20 through the crotch region 28 and into the back waist region 22. The transverse direction 50 is perpendicular to the longitudinal direction 48. The chassis 12 includes an outer shell 36 and may further include waist elastic, leg elastic, or both. Referring again to FIG. 1, the chassis 12 is illustrated with a waist elastic 38 attached to the outer shell 36 and encircling the waist opening 16 and leg elastics 40 attached to the outer shell 36 and encircling each of the leg openings 18.

In various embodiments, the outer shell may be made of a single piece of material or multiple pieces of material. In some embodiments, the outer shell may be made of two or more pieces of material.

In various embodiments, the component pieces of the outer shell may be joined together in any suitable manner. For example, the front component 24 may be joined to the back component 31 at a crotch seam. Additionally, one or both of the lateral side edges of the back component may be joined to one or both of the lateral side edges of the front component at one or more side seams to define a three-dimensional garment. Specifically, the lateral side edges 25 of the back component 31 may be joined with the lateral side edges 27 of the front component 24 at side seams 26 to define the leg openings 18 and the waist opening 16 of the containment pant 10 as illustrated in FIG. 1.

In various embodiments, the side seams and/or the crotch seams may be formed using any suitable means such as ultrasonic bonding, thermal bonding, adhesive bonding, pressure bonding, sewing, and the like and combinations thereof. In some embodiments, the side seams and/or the crotch seam may be formed by sewing the component pieces of the outer shell using thread and any suitable stitch pattern or combination of patterns. In some embodiments, the side seams and/or crotch seams may be formed using a flatlock stitch.

In various embodiments, the waist elastic and/or leg elastic may be joined with the outer shell using any suitable means such as ultrasonic bonding, thermal bonding, adhesive bonding, pressure bonding, sewing, and the like and combinations thereof. In some embodiments, the waist elastic and/or leg elastic may be sewed to the outer shell using thread and any suitable stitch pattern or combination of patterns. For example, FIGS. 1-3 representatively illustrate the waist elastic 38 joined with the outer shell 36 at a sewn waist elastic seam 39 and the leg elastics 40 joined with the respective outer shells 36 and 37 at sewn leg elastic seams 41. In some embodiments, the waist elastic and/or leg elastic may be sewed to the outer shell using a cover stitch.

Inside the chassis 12 is the sling 14, which includes a fluid-impervious base sheet 30 and at least first containment flap 32 and second containment flap 34 joined with the base sheet 30 to create a fluid-impervious sling 19. The fluid-impervious sling 19 is adapted to house a removable absorbent insert and contain fluid until it can be taken into the absorbent insert. The fluid-impervious sling 19 is drapeable and is designed to conform and gasket against the body of the wearer.

Figure 4:
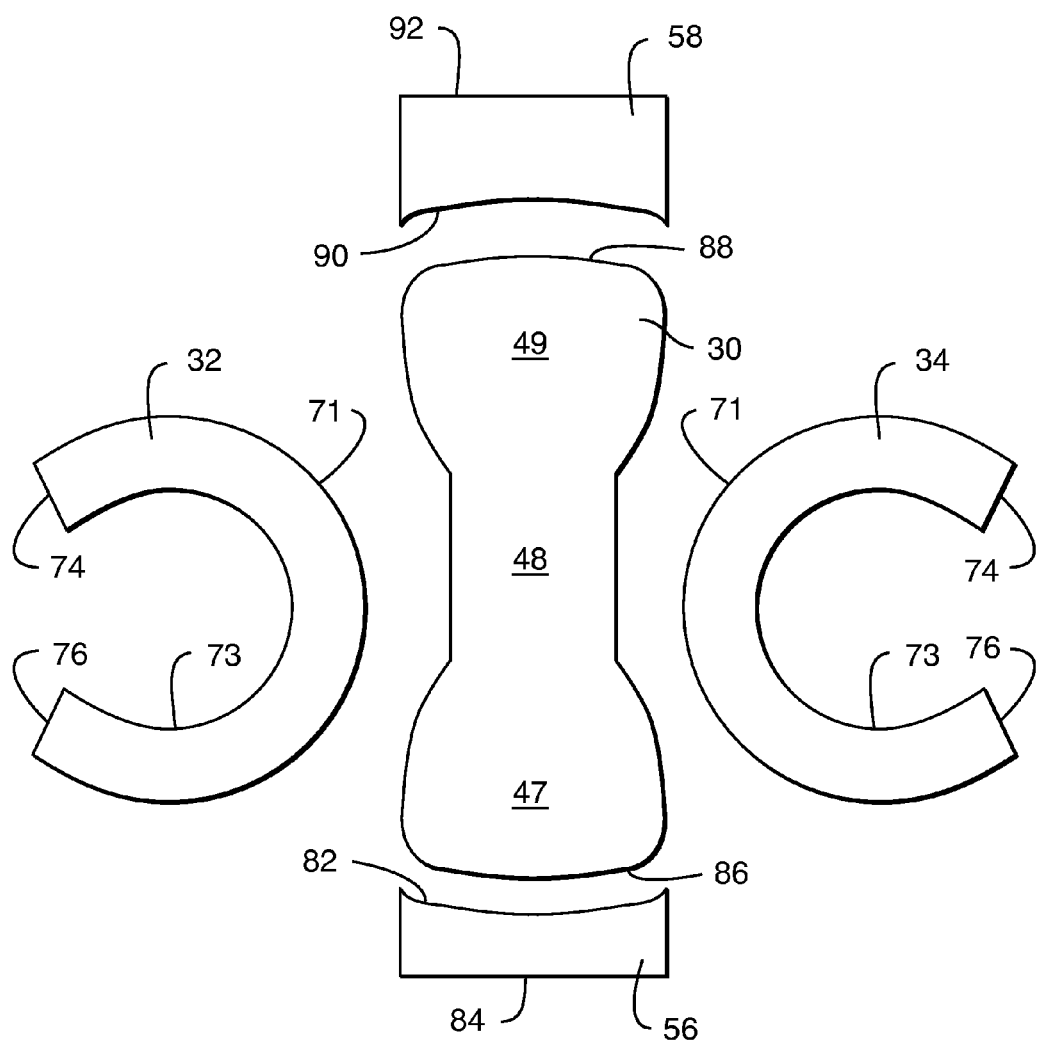
FIG. 4 representatively illustrates a top plan view of component parts of another exemplary pouch and sling of the present invention FIG. 5 representatively illustrates a fully constructed sling made from the component parts of FIG. 4.

The sling and a fluid-impervious pouch may be constructed with a first containment flap, a second containment flap, a base sheet, a first transition, and a second transition. For example, referring now to FIG. 4, a top plan view of the component parts of another exemplary pouch and sling are representatively illustrated. A fully constructed sling 14 made from the component parts of FIG. 4 is representatively illustrated in FIG. 4. The component parts include a first side containment flap 32, a second side containment flap 34, a base sheet 30, a first transition 56, and a second transition 58. The base sheet 30 may have a curvilinear shape wherein the base sheet defines a first portion 47, a second portion 48, and a third portion 49. In the illustrated embodiment, the first portion 47 has curvilinear side edges and a maximum width that is greater than the maximum width of the second portion 48. Additionally, the third portion 49 has curvilinear side edges and a maximum width that is greater than the maximum width of the second portion 48. The second portion 48 has relatively straight and parallel side edges. The base sheet 30 defines an absorbent facing surface and a chassis facing surface.

In various embodiments, the side containment flaps ideally have a curved cut. For example, the first side containment flap 32 and the second side containment flap 34 of FIG. 4 are illustrated as having a curved cut. While not wishing to be bound by theory, it is believed that the curved cut containment flaps facilitate closer alignment with the natural curvature of the wearer's body. As such, it is believed that a more comfortable and better fit can be achieved to reduce leakage during use.

The first side and second containment flaps 32 and 34 each define a proximal portion 71 and a distal portion 73. A first end 74 of the first containment flap 32 is joined with a first end 74 of the second containment flap 34 to define a first bridging seam 78. Likewise, the second end 76 of the first containment flap 32 and the second end 76 of the second containment flap 34 are joined to define a second bridging seam 78.

Figure 5:
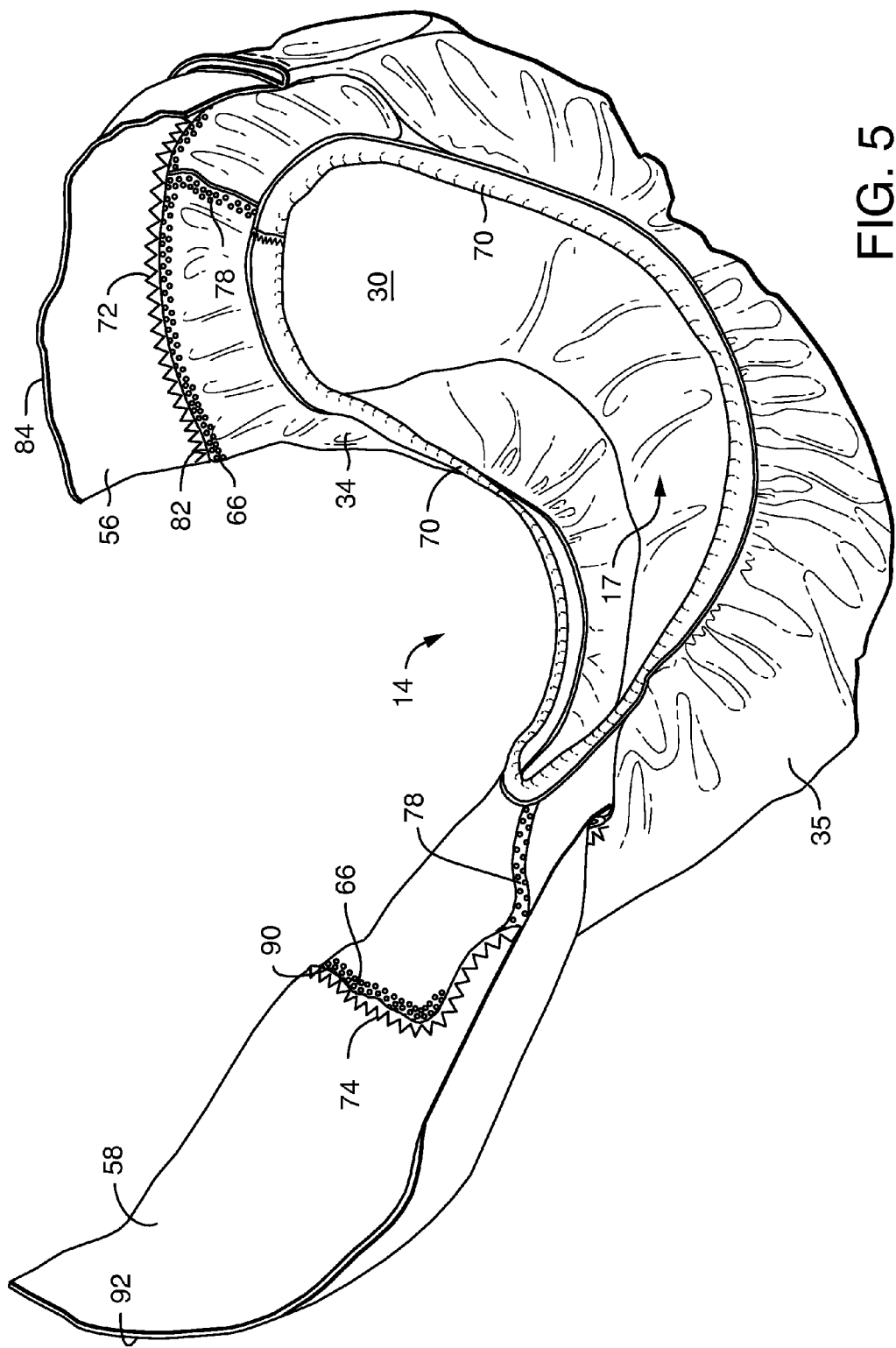

The proximal portions 412 of each containment flap 32 and 34 is joined with the base sheet 30 to create a containment flap seal 466 and define a fluid-impervious pouch 17 as illustrated in FIG. 5. In some embodiments, the containment flaps may further include one or more elastics. For example, as illustrated in FIG. 14, the distal portion 73 of each of the containment flaps 32 and 34 further includes a containment flap elastic 470.

In various embodiments, the fluid-impervious pouch 17 may be incorporated into any suitable sling and/or chassis using integrated transitions, discrete transitions, or combinations thereof. In various embodiments, the fluid-impervious pouch 17 may be incorporated into any suitable sling and/or chassis using only a transition joined with the front waist region, only a transition joined with the back waist region, or neither. In FIG. 5 the fluid-impervious pouch 17 is joined with the first transition 56 and the second transition 58 to define the sling 14. The first transition 56 defines a first edge 82 and a second edge 84. Likewise, the second transition 58 defines a first edge 90 and a second edge 92. The base sheet 30 defines a first edge 86 and a second edge 88. Desirably, the first edge 86 and the second edge 88 of the base sheet 30 define curved convex shapes. The first edge 86 of the base sheet 30 is joined with the first edge 82 of the first transition 56 to define a first junction 72. The second edge 84 of the first transition 56 defines a curved shape to match the first edge of the base sheet 30. Likewise, the second edge 88 of the base sheet 30 is joined with the first edge 90 of the second transition 58 to define a second junction 74. The first edge 90 of the second transition 58 defines a curved shape to match the second edge 88 of the base sheet 30. The first and second junction 72 and 74 may include adhesive bonding, thermal bonding, ultrasonic bonding, pressure bonding, and the like, and combinations thereof.

In various embodiments, the sling 14 of FIG. 5 can be joined with any suitable chassis to form a containment pant. In various embodiments, the sling 14 may be joined with a chassis such that the first transition is located in either the front waist region or the back waist region of the chassis and the second transition is located in the opposite region of the chassis. For example, referring now to FIGS. 2 and 3, an exemplary containment pant 10 having a chassis 12 and the sling 14 is representatively illustrated. FIG. 2 is a side perspective view of the containment pant 10 with the chassis 12 partially severed to illustrate the attachment of the sling 14 in the back waist region 22. Specifically, the second transition 58 is joined with the back waist region 22 of the chassis 12 at a back sling seam 43. FIG. 3 is a side perspective view of the containment pant 10 with the chassis 12 partially severed to illustrate the attachment of the sling 14 in the front waist region 20. Specifically, the first transition 56 is joined with the front waist region 20 of the chassis 12 at a front sling seam 45.

In various embodiments, the pouch floor may define any suitable shape. For example, the pouch floor may have a symmetric shape about the transverse centerline or may have an asymmetric shape about the transverse centerline. In various embodiments, the pouch floor may have a dog-bone-shape, hourglass-shape, T-shape, rectangular shape, or the like.

In various embodiments, the pouches of the present invention may be joined with one or more transitions in any suitable manner. For example, the pouches may be joined with the transitions by sewing, ultrasonic bonding, thermal bonding, adhesive bonding, seam taping, and the like, and combinations thereof. In some embodiments, the transitions may be joined with the pouches by sewing, using any suitable stitch or combination of stitches. For example, in some embodiments, the transitions may be attached to the pouches using a single needle stitch followed by a top stitch.

In some embodiments, the pouches may be constructed such that extra material is available for attaching the transitions without breaching the fluid-impervious integrity of the pouch. For example, in some embodiments, the containment flap may be joined to the base sheet at the containment flap seal. The containment flap seal may be positioned such that a portion of the containment flap material and/or the base sheet material is available for attaching to the first and/or second transition while maintaining the integrity of the fluid-impervious pouch.

In some embodiments, the sling is minimally attached to the chassis to maximize the fit and natural movement of the chassis. In some embodiments, the sling is attached to the chassis via the first transition and/or the second transition. In various embodiments, the first transition may be joined with the front waist region at the front sling seam and the second transition may be joined with the back waist region at the back sling seam. In other embodiments, the first transition may be joined with the back waist region at the back sling seam and the second transition may be joined with the front waist region at the front sling seam. The first transition and/or the second transition may be joined to any suitable portion of the front waist region and/or the back waist region. For example, the first transition and/or the second transition may be joined at the waist elastic seam in the front waist region and/or the back waist region. Additionally or alternatively, the first transition and/or the second transition may be joined to the outer shell in the front waist region and/or the second waist region. In some embodiments, the first transition and/or the second transition may be integral with the chassis. In these embodiments, the integral transition is joined with the pouch using any suitable method, including those described herein. In some embodiments, the first transition and/or the second transition may be integral with the shell of the chassis.

In some of the embodiments, the sling 14 may be attached to the chassis 12 via an attachment mechanism. Various embodiments may be utilized for the attachment mechanism to attach the chassis 12 as long as the sling 14 is secured to the chassis to enable movement of the sling with the body and stay in place.

Figure 6:
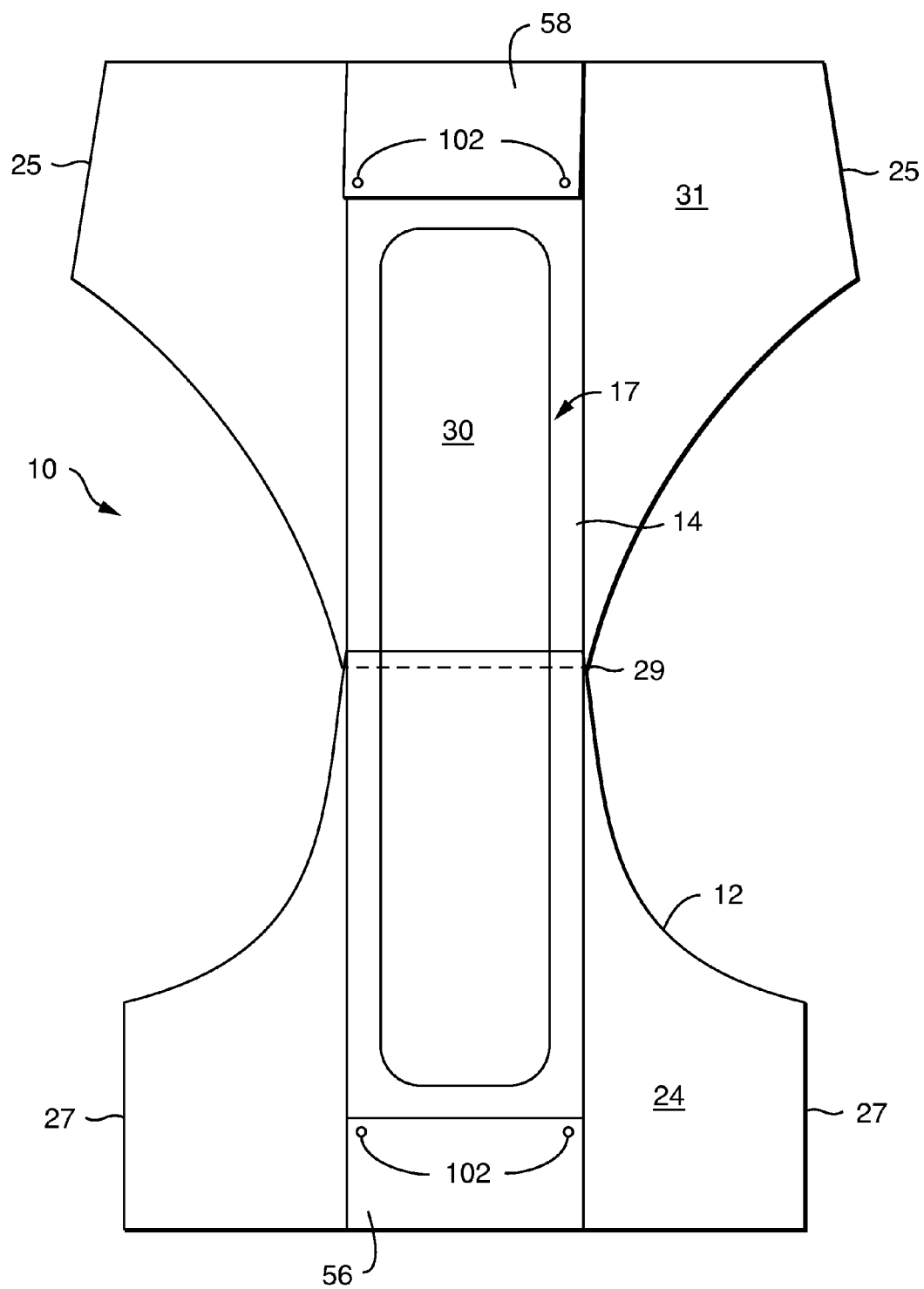
FIG. 6 illustrates representatively illustrate a top plan view of the exemplary containment illustrating one embodiment of an attachment mechanism to secure the sling to the outer chassis.

In one embodiment as illustrated in FIG. 6, the attachment mechanism may be an attachment bond 102 in the first transition 56 or second transition 58 adjacent to the sling 14. By placing the attachment bonds 102 adjacent to the sling 14, the chassis 12 will provide stretch to the first transition 56 or the second transition 58 materials increasing pouch 17 stability. The attachment bond 102 may include a single attachment bond or multiple attachment bonds. In various embodiments, the attachment bond 102 may be attached to the chassis 12 using any suitable means including ultrasonic bonded, thermal bonded, adhesive bonded, pressure bonded, and the like, and combinations thereof.

As illustrated in FIG. 6, the attachment bond 102 may include both a first attachment bond and a second attachment bond adjacent lateral side edges of the first transition 56 or the second transition 58. By placing the attachment bonds 102 adjacent lateral side edges of the first transition 56 or the second transition 58, the chassis 12 will provide stretch to the first transition 56 or the second transition 58 materials increasing pouch 17 width and stability. As a result, the fluid impervious pouch 17 will not collapse inward improving fit on a user and therefore reducing leakage in the product. Optionally, the attachment bond 102 includes a first attachment bond and a second attachment bond adjacent lateral side edges of both the first transition 56 and the second transition 58.

In some embodiment, the bonded attachment 102 may be hidden on the chassis 12 with appliques, hidden in piping and hidden within graphics to not detract from the overall appearance of the pant 10.

Figure 7:
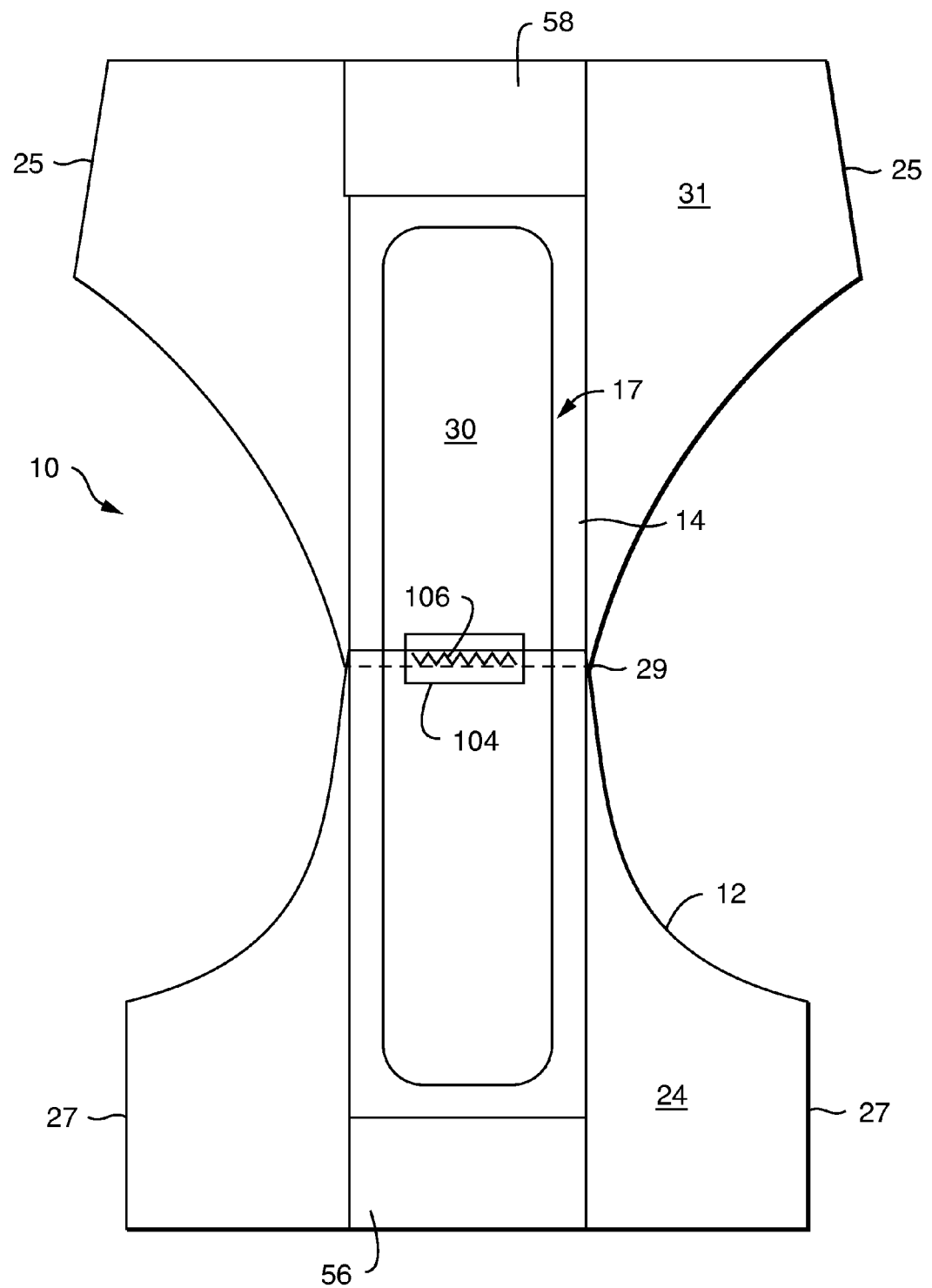
FIG. 7 illustrates representatively illustrate a top plan view of the exemplary containment illustrating another embodiment of an attachment mechanism to secure the sling to the outer chassis.
Figure 8:
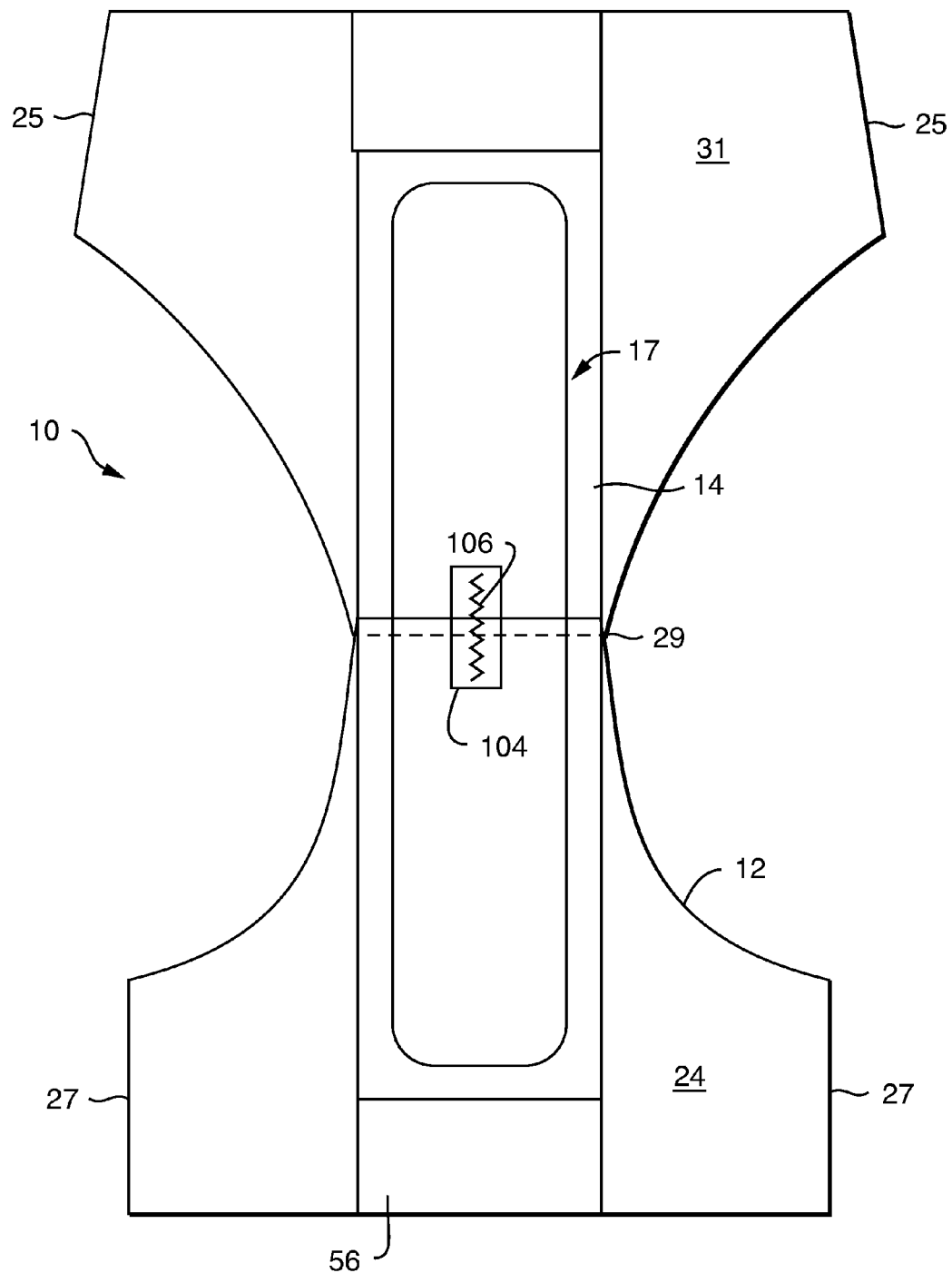
FIG. 8 illustrates representatively illustrate a top plan view of the exemplary containment illustrating another embodiment of an attachment mechanism to secure the sling to the outer chassis.

In one embodiment as illustrated in FIGS. 7-8, the attachment mechanism attaching the sling 14 to the chassis 12 in the crotch region 28 may be a bonded attachment 104 and an attachment elastic material 106. The sling 14 and elastic attachment material 104 may be attached via a bonded attachment 104 to the chassis in the crotch region 28 by any suitable means. For example, the bonded attachment 104 may be sewed, ultrasonic bonded, thermal bonded, adhesive bonded, pressure bonded, and the like, and combinations thereof.

In these embodiments, the attachment elastic material 106 is utilized to ensure against leakage. The attachment elastic material 106 may be discrete pieces of material that are joined with the pouch 17 of the sling using any suitable means. For example, in some embodiments, the attachment elastic material 104 may be discrete pieces of material that are ultrasonically bonded to the base 30 of the fluid-impervious pouch 17.

As illustrated in FIG. 7, the attachment elastic material 106 has stretch in the transverse direction allowing for the attachment elastic material 106 to stretch across the width of the pouch 17. Having stretch in the transverse direction in the pouch 17 helps the absorbent insert to stay in place within the pouch 17, increases a bucket within the pouch 17 to help with leakage, and maintains pouch 17 stability.

As illustrated in FIG. 8, the attachment elastic material 106 has stretch in the longitudinal direction allowing for the attachment elastic material 106 to stretch across the length of the pouch 17. Having stretch in the longitudinal direction in the pouch 17 helps the absorbent insert fit better against the body and maintains pouch 17 stability.

Figure 9:
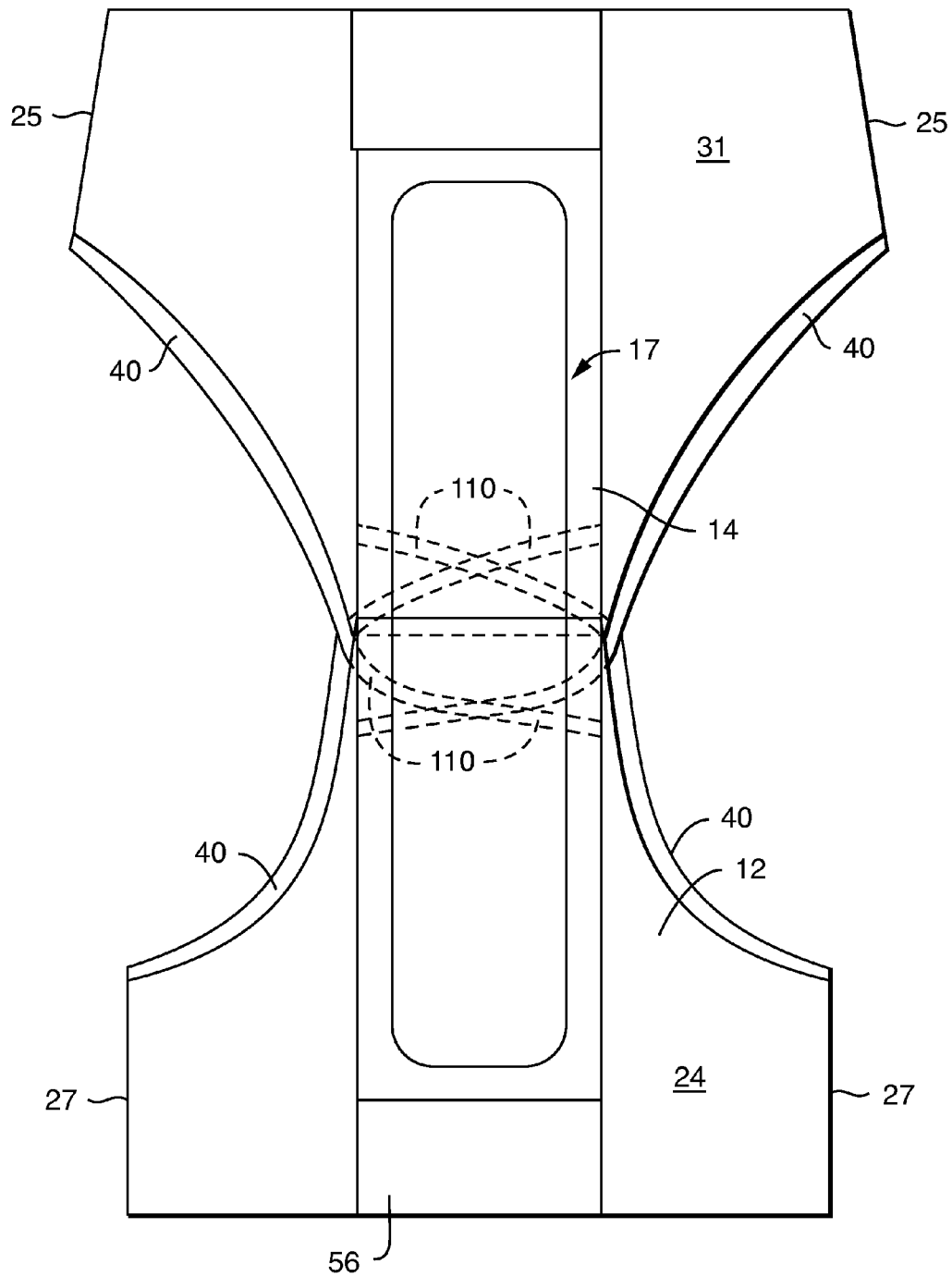
FIG. 9 illustrates representatively illustrate a top plan view of the exemplary containment illustrating another embodiment of an attachment mechanism to secure the sling to the outer chassis.

In another embodiment illustrated in FIG. 9, the attachment mechanism attaching the sling 14 to the chassis 12 in the crotch region 28 may be elastics 110 extending from leg openings and attaching to the sling 14 in a crotch region 28. The elastics are any type of elastic material known to one skilled in the art. As illustrated, the elastics comprise leg elastics 110 extending from leg openings may be attached via a bonded attachment 104 to the sling 14 in the crotch region 28 by any suitable means. For example, the bonded attachment 104 may be sewed, ultrasonic bonded, thermal bonded, adhesive bonded, pressure bonded, and the like, and combinations thereof.

As illustrated in FIG. 9, the pair of leg elastics 110 extending from leg openings and attaching to the sling 14 in a crotch region 28 extend from the leg opening on one side of the pant 10 to the lateral side edge of the sling 14 on the other side of the pant 10. In some embodiments, the pair of leg elastics 110 extending from leg openings and attaching to the sling 14 in a crotch region overlap 28.

In some embodiments, the chassis 12 is formed a front component 24 joined to the back component 31 at a crotch seam 29. In this embodiment, a pair of leg elastics 110 extend from both the front component 24 and back component 31, the leg elastics 110 attaching to the sling 14 in a crotch region 28. The pair of leg elastics 110 extending from both the front component 24 and back component 31 extend from the leg opening on one side of the pant 10 to the lateral side edge of the sling 14 on the other side of the pant 10. In some embodiments, the pair of leg elastics 110 extending from the front component 24 and attaching to the sling 14 overlap and the pair of leg elastics 110 extending from the back component 31 and attaching to the sling 14 in a crotch region overlap.

In various embodiments, at least one of the materials of the containment pant is treated to be more fluid impervious. For example, in any of the embodiments described herein, at least one of the shell, waist elastic, leg elastic, transitions, base sheet, containment flaps, containment flap elastic, and thread are treated to be more fluid impervious. In various embodiments, the treatment may include coating the materials in any suitable manner using a durable water resistant treatment. In some embodiments, the durable water resistant treatment may include a polymer coating. In some embodiments, the base sheet and/or the containment flaps may include a fabric laminated with polyurethane wherein the fabric side of the base sheet is treated with a durable water resistant treatment. In some embodiments, the base sheet and the containment flaps may be made from a woven polyester fabric treated with a durable water resistant treatment and laminated with a polyurethane sheet. In some embodiments, the thread used to join the containment flap elastic to the containment flaps may be treated with a durable water resistant treatment.

In some embodiments, the containment pants of the present invention may be adapted to fit a wide range of sizes. In some embodiments, an exemplary containment pant may be adapted to fit children weighing between 38 and 65 pounds. In some embodiments, an exemplary containment pant may be adapted to fit children weighing between 60 and 120 pounds. To facilitate such a wide range of weight and maintain proper fit, the containment pants of the present invention may be adapted in the waist, hip, and/or legs to extend up to about 100% while still providing sufficient retractive force to hold the pants securely against the body at donning, during use, and after insult.

Figure 10:
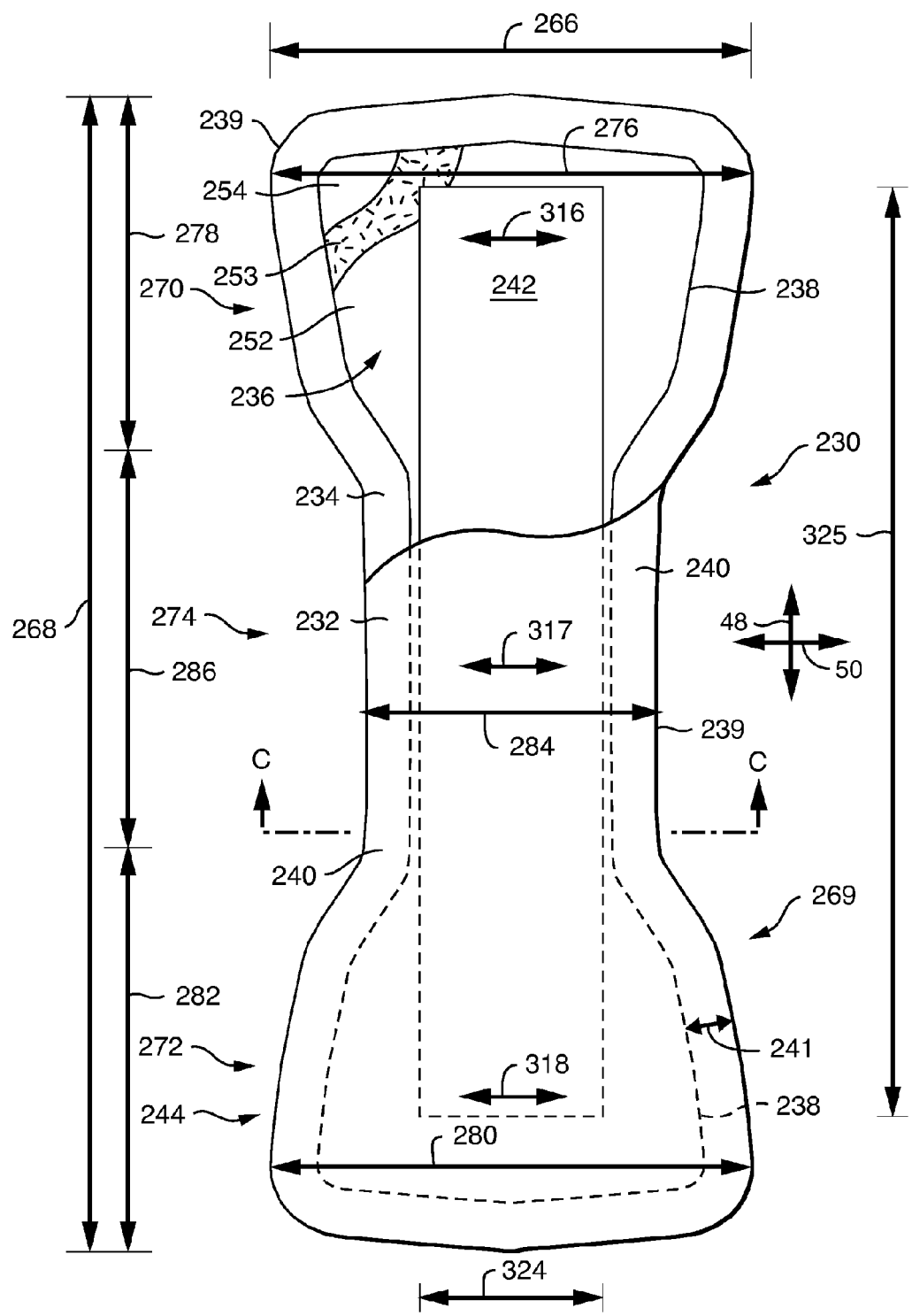
FIG. 10 representatively illustrates a top plan view of an exemplary absorbent insert of the present invention with portions cut away to illustrate underlying structure.
Figure 11:
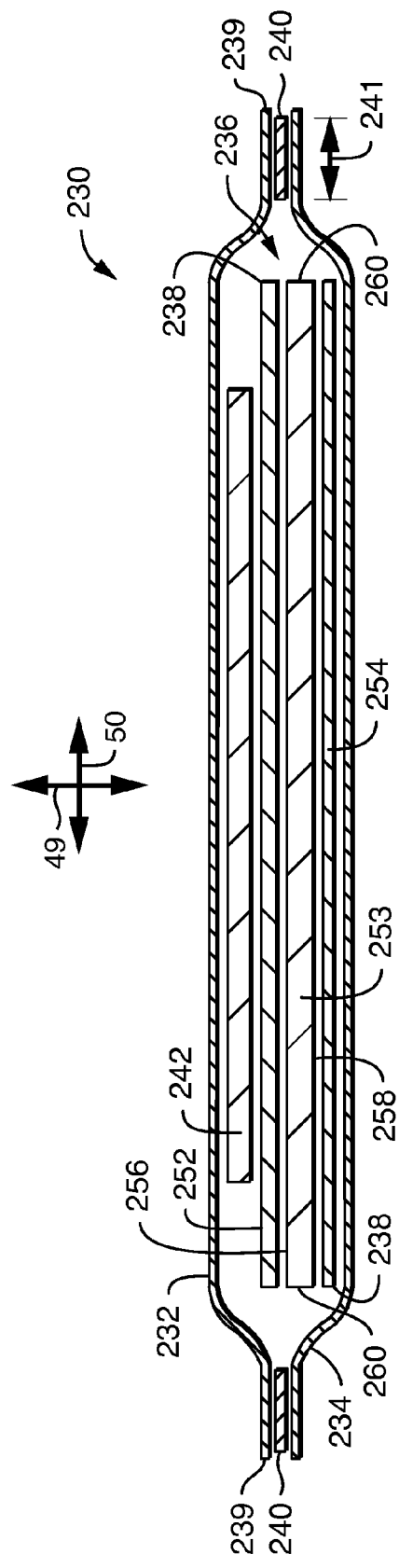
FIG. 11 representatively illustrates a cross sectional view of the absorbent insert of FIG. 11 taken along the line C-C.

Referring now to FIGS. 10 and 11, a first exemplary absorbent insert 230 is representatively illustrated. FIG. 10 is a top plan view of the absorbent insert 230 with portions cut away to better illustrate underlying structure. FIG. 11 is an expanded cross-sectional view of the absorbent insert of FIG. 10 taken along the line C-C. The absorbent insert 230 defines a longitudinal-direction 48, a relatively shorter, transverse direction 50, and a thickness direction 49. The transverse direction extends generally perpendicular to the longitudinal direction, and the thickness or z-direction extends generally perpendicular to both the longitudinal-direction and transverse direction.

The absorbent insert 230 includes a first sheet 232 and a second sheet 234 in facing relation with the first sheet 232. The absorbent insert 230 also includes an absorbent core 236 positioned between the first sheet 232 and the second sheet 234. The absorbent core 236 defines a core perimeter 238, and the first sheet 232 and the second sheet 234 extend beyond the core perimeter 238, and are joined together to form a perimeter seal 240. The outer extent of the first sheet 232 and/or the second sheet 234 defines the absorbent insert perimeter 239. The absorbent insert perimeter 239 in turn defines an absorbent insert area 269.

The absorbent insert 230 defines an absorbent insert width 266 and an absorbent insert length 268. The absorbent insert 230 defines a first end section 270, a second end section 272, and a central section 274 in the longitudinal direction 48. The central section 274 extends between the first end section 270 and the second end section 272. The first end section 270 defines a first end section width 276 and a first end section length 278. The second end section 272 defines a second end section width 280 and a second end section length 282. The central section 274 defines a central section width 284 and a central section length 286. The first end section length 278 plus the second end section length 282 plus the central section length 286 equals the absorbent insert length 268. The widths of the various sections are measured in the transverse direction 50 and the lengths of the various sections are measured in the longitudinal direction 48.

In an embodiment adapted for use by a child weighing 60 to 120 pounds, the absorbent insert length may be 425 to 475 mm, or 430 to 450 mm, or about 440 mm. In an embodiment adapted for use by a child weighing 38 to 65 pounds, the absorbent insert length may be 375 to 425 mm, 390 to 410 mm, or about 400 mm. In various embodiments, the first end section length may equal the central section length which may equal the second end section length. In other embodiments, the first end section length may equal the second end section length and the central section length may be different. For example, the first end section length may be about 35% the absorbent insert length, the second end section length may be about 35% the absorbent insert length, and the central section length may be about 30% the absorbent insert length. In another example, the first end section length may be about 30% the absorbent insert length, the second end section length may be about 30% the absorbent insert length, and the central section length may be about 40% the absorbent insert length.

In various embodiments, the absorbent insert may have a width that varies at different points along the longitudinal direction. For example, as illustrated in FIG. 10, the absorbent insert 230 has a variable width at different points along the longitudinal direction. In this embodiment, the first end section 270 and the second end section 272 have a maximum width that is greater than the maximum width of the central section 274. For example, in some embodiments, the first end section and the second end section may have a maximum width of about 160 to 210 mm, 170 to 200 mm, 180 to 190 mm or about 186 mm. In these embodiments, the central section may have a maximum width of about 90 to 130 mm, about 100 to 120 mm, or about 114 mm.

In various embodiments, the first end section, the second end section, and/or the central section may have a variable width at different points along the longitudinal direction or may have a consistent width at different points along the longitudinal direction. In some embodiments, the first end section and the second end section may have variable width at different points along the longitudinal direction and the central section may have a consistent width at different points along the longitudinal direction as illustrated in FIG. 10. For examples, the first end section and the second end section may have a width that varies from 186 mm at the maximum to 114 mm at the minimum. In these embodiments, the central section may have a consistent width of about 114 mm.

The absorbent insert 230 also defines an absorbent insert area 269. In various embodiments, the absorbent insert area 269 may be any suitable value. For example, in embodiments adapted for use by a child weighing 60 to 120 pounds, the absorbent insert area 269 may be about 65,000 mm$^2$. In embodiments adapted for use by a child weighing 38 to 65 pounds, the absorbent insert area 269 may be about 57,600 mm$^2$.

In an embodiment adapted for use by a child weighing 60 to 120 pounds, the absorbent core length may be 350 to 450 mm, 375 to 425 mm, 390 to 410 mm, or about 400 mm. In an embodiment adapted for use by a child weighing 38 to 65 pounds, the absorbent core length may be 340 to 380 mm, 350 to 370 mm, or about 360 mm. In various embodiments, the first end section length may equal the central section length which may equal the second end section length. In other embodiments, the first end section length may equal the second end section length and the central section length may be different. For example, the first end section length may be about 25% the absorbent core length, the second end section length may be about 25% the absorbent core length, and the central section length may be about 50% the absorbent core length. In another example, the first end section length may be about 30% the absorbent core length, the second end section length may be about 30% the absorbent core length, and the central section length may be about 40% the absorbent core length.

In various embodiments, the first end section, the second end section, and/or the central section may have a variable width at different points along the longitudinal direction or may have a consistent width at different points along the longitudinal direction. In some embodiments, the first end section and the second end section may have variable width at different points along the longitudinal direction and the central section may have a consistent width at different points along the longitudinal direction as illustrated in FIG. 11. In some embodiments, the first end section and the second end section may have a width that varies from 145 mm at the maximum to 75 mm at the minimum. In these embodiments, the central section may have a consistent width of about 75 mm.

The absorbent core also defines an absorbent core area. In various embodiments, the absorbent core area may be any suitable value. For example, in an embodiment adapted for use by a child weighing 60 to 120 pounds, the absorbent core area may be about 42,000 mm$^2$. In an embodiment adapted for use by a child weighing 38 to 65 pounds, the absorbent core area may be about 36,300 mm$^2$.

In various embodiments, the perimeter seal may have any suitable width and may be formed by any suitable method. Referring again to FIGS. 10-11, the perimeter seal width 241 is representatively illustrated. In some embodiments, the perimeter seal width may be at least 5, at least 10, at least 15, or at least 20 mm. The perimeter seal may include adhesive bonding, thermal bonding, ultrasonic bonding, pressure bonding, and the like, and combinations thereof. In some embodiments, the first sheet may be joined to the second sheet at the perimeter seal via adhesive bonding and the perimeter seal width may be at least 20 mm. In other embodiments, the first sheet may be joined to the second sheet at the perimeter seal via ultrasonic bonding and the perimeter seal width may be at least 10 mm.

In some embodiments, the absorbent insert may be substantially devoid of fluid-impervious materials. In some embodiments, the absorbent insert does not include a fluid-impervious barrier layer. In comparison, many absorbent articles include a fluid-impervious back sheet or baffle which is provided to prevent fluid from contacting the clothes of the wearer or a delay layer which is provided to slow or divert the fluid. In the present invention, the absorbent insert is positioned within the fluid-impervious pouch and thus does not require a fluid-impervious layer as part of the absorbent insert. Additionally, this design is believed to be beneficial in some embodiments over conventional inserts because fluid can be absorbed into the absorbent insert along the entire pad, including the body-facing surface, the garment-facing surface, and the sides. Additionally, the omission of a fluid-impervious layer eliminates the risk of fluid being trapped between the fluid-impervious pouch and the absorbent insert which might cause leaking during use or leaking when removing the absorbent insert from the pouch.

In some embodiments, the absorbent insert may further include one or more intake layers. For example, the absorbent insert 230 of FIGS. 10 and 11 is illustrated with a first intake material 242 positioned between the first sheet 232 and the absorbent core 236. In some embodiments, the absorbent insert may additionally or alternatively include a second intake material.

In various embodiments, the first intake material and/or the second intake material may have any suitable length, width, or shape. For example, referring again to FIG. 10, the first intake material 242 defines an intake material width 324 and an intake material length 325. In various embodiments, the intake material width may be 50 to 80 mm or about 62 mm. In these embodiments, the intake material width may be at least 70%, 80%, or 90% the second reference width 317 of the absorbent core. In some embodiments, the intake material width may be about 84% the second reference width 317 of the absorbent core.

In some embodiments, the intake material length may be about 325 to 375 mm, 340 to 360 mm, or about 355 mm. In these embodiments, the intake material length may be at least 70%, 80%, or 90% the absorbent core length. In some embodiments, the intake material length may be about 88% the absorbent core length.

In various embodiments, the intake materials may be rectangular as illustrated in FIG. 10 or may be any other suitable shape. For example, in various embodiments, the intake materials may be shaped similarly to the absorbent insert and/or the absorbent core.

In various embodiments, any of the absorbent inserts of the present invention may include absorbent cores having absorbent material and one or more wrap sheets. For example, in some embodiments, the absorbent cores may include a single wrap sheet folded around the longitudinal side edges of the absorbent material and overlapping upon itself to form a fully wrapped absorbent core. In other embodiments, the absorbent core may include two wrap sheets. In these embodiments, one of the wrap sheets may be primarily positioned on a first-facing surface of the absorbent material. The other wrap sheet may be primarily positioned on the second-facing surface of the absorbent material. In these embodiments, the wrap sheet on the second-facing surface may extend to the longitudinal side edges of the absorbent material, may wrap around the longitudinal side edges of the absorbent material, or may extend to the first-facing surface of the absorbent material. Likewise, the wrap sheet on the first-facing surface may extend to the longitudinal side edges of the absorbent material, may wrap around the longitudinal side edges of the absorbent material, or may extend to the second-facing surface of the absorbent material. The wrap sheets may overlap themselves or may overlap each other.

Referring again to FIG. 11, the absorbent core 236 is representatively illustrated with a first wrap sheet 252 positioned on a first-facing surface 256 of the absorbent material 253. The first wrap sheet 252 extends between the longitudinal side edges 260 of the absorbent material 253. The absorbent core 236 also includes a second wrap sheet 254 positioned on a second-facing surface 258 of the absorbent material 253. The second wrap sheet 254 extends between the longitudinal side edges 260 of the absorbent material 253.

In various embodiments, the first sheet and the second sheet may be made of the same material or may be different. In some embodiments, the first sheet and the second sheet may have the same basis weight or may be different. The first sheet and/or the second sheet may be fluid permeable and may be made of substantially hydrophobic fibrous material. For example, the first sheet and/or the second sheet may be a spunbond web composed of synthetic polymer filaments. In some embodiments, the first sheet and/or the second sheet may be a meltblown web or a bonded-carded-web composed of synthetic polymer filaments. Suitable synthetic polymers include, for example, polyethylene, polypropylene, polyester, and the like, and combinations thereof. In some embodiments, both the first sheet and the second sheet are spunbond polypropylene nonwoven webs having an individual basis weight of about 15 gsm. In some embodiments, the first sheet and/or the second sheet may be treated with surfactants to adjust the degree of hydrophobicity and wettability. In some embodiments, the first sheet and/or the second sheet may be embossed, apertured, slit, or otherwise mechanically worked.

The absorbent core typically includes absorbent material composed of airlaid, cellulosic fibers commonly referred to as wood pulp fluff. Other natural fibers, such as cotton, may also be employed to form the absorbent core. The absorbent core can have a density ranging from about 0.18-0.30 grams/cc. This density range allows the absorbent core to be sufficiently flexible to readily conform to the body of the wearer yet maintain sufficient rigidity for insertion into the pouch. In some embodiments, the absorbent core may have a density of about 0.24 grams/cc. The absorbent core may alternatively or additionally include a coform material composed of a mixture of cellulosic fibers and synthetic polymer fibers. For example, the coform material may be composed of an airlaid blend of cellulosic fibers and meltblown polyolefin fibers, such as polyethylene and/or polypropylene fibers. In addition, the absorbent core may have a dry thickness of about 1 to 5 mm or about 2 mm, as measured under a restraining pressure of 0.068 psi (0.47 kPa).

The absorbent core may also include an effective amount of an inorganic or organic high-absorbency (e.g., superabsorbent) material to enhance the absorptive capacity of the absorbent body. For example, the absorbent core can contain 5-95 weight percent high-absorbency material, and preferably includes about 30-70, 40-60, or about 50 weight percent of the high-absorbency material to provide more efficient performance. In some embodiments, the absorbent core can include equal amounts of fluff and superabsorbent. For example, in some embodiments, the absorbent core may include at least 14, at least 15, at least 16, at least 17, at least 18, or at least 19 grams of superabsorbent. In some embodiments, the absorbent core may include at least 14, at least 15, at least 16, at least 17, at least 18, or at least 19 grams of fluff. In some embodiments, the absorbent core may include about 19 grams of superabsorbent and about 19 grams of fluff. In other embodiments, the absorbent core may include about 17 grams of superabsorbent and about 17 grams of fluff.

Suitable inorganic high-absorbency materials include, for example, absorbent clays and silica gels. Organic high-absorbency materials can include natural materials, such as agar, pectin, guar gum and peat moss, as well as synthetic materials, such as synthetic hydrogel polymers. Such hydrogel polymers include, for example, carboxymethylcellulose, alkali metal salts of polyacrylic acids, polyacrylamides, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, and isobutylene maleic anhydride copolymers, and mixtures thereof. The hydrogel polymers are preferably lightly cross-linked to impart desired levels of water insolubility to the material.

In some embodiments, the wrap sheet may be woven or non-woven material and may be made of any suitable material. For example, the wrap sheet may be made of polypropylene, cellulosic tissue, and the like, and combinations thereof. In some embodiments, the wrap sheet may be nonwoven material made from spunbond polypropylene and may have a basis weight of about 10 gsm.

The intake layer or layers help to decelerate and diffuse surges or gushes of fluid that can be rapidly introduced into the absorbent insert. Desirably, the intake layer can rapidly accept and temporarily hold the fluid prior to releasing the fluid into the absorbent core of the absorbent insert. In some embodiments, the intake layer may be a through air bonded carded web composed of 40% hollow polypropylene fibers (6 denier) and 60% bicomponent fibers (6 denier) (bicomponent sheath: polypropylene core). In various embodiments, the intake layer may have any suitable basis weight. For example, the intake layer may have a basis weight of at least 30, at least 50, at least 75, at least 100, or at least 125 grams per square meter (gsm). In some embodiments, the intake layer may have a basis weight of about 128 gsm. Other examples of suitable intake layers are described in U.S. Pat. No. 5,486,166; U.S. Pat. No. 5,490,846; and U.S. Pat. No. 5,820,973. The entire disclosures of these patents are hereby incorporated by reference herein to the extent they are consistent (i.e., not in conflict) herewith.

In some embodiments, the absorbent insert may have a first intake layer and a second intake layer. In some embodiments, the first intake layer may be the same material as the second intake layer or may be different. In some embodiments, the first intake layer may have the same basis weight as the second intake layer or may be different.

In some embodiments, the absorbent inserts of the present invention may be characterized, at least in part, by specific absorbent properties. For example, in some embodiments, the absorbent inserts may have a total absorbent capacity of at least 600 grams, at least 650 grams, at least 700 grams, or at least 750 grams of 0.9% saline solution. In some embodiments, the absorbent inserts may have an absorbent capacity of about 740 grams or about 827 grams. The total absorbent capacity of the absorbent inserts may be determined by using the Retention Capacity Test Method. This test method measures the amount of fluid retained by an absorbent insert under external pressure. An initial weight of the absorbent insert is measured and then the absorbent insert is submerged in a 0.9% saline solution for 20 minutes. After the saturation time, 0.5 psi pressure is applied across the entire absorbent insert for 5 minutes and the excess saline solution is allowed to drain. After the pressure time, the weight of the saturated absorbent insert is measured. The total absorbent capacity is calculated as the saturated weight minus the initial weight.

In some embodiments, the absorbent inserts may be characterized by total absorbent capacity as a ratio of crotch width. In some embodiments, the products designed for wearers having a weight of 60 to 120 pounds may have an absorbent capacity of about 827 grams and a crotch width of about 74 mm. In other embodiments, the products designed for wearers having a weight of 38 to 65 pounds may have an absorbent capacity of about 740 grams and a crotch width of about 74 mm. Thus, in some embodiments, the ratio of total absorbent capacity to crotch width may be at least 9 g/mm, at least 10 g/mm, or at least 11 g/mm.

The absorbent inserts of the present invention may be provided in any suitable manner. For example, the absorbent inserts may be folded, stacked, wrapped, compressed, or the like, and combinations thereof. In some embodiments, the absorbent inserts may be individually wrapped in a wrapper. In some embodiments, the absorbent inserts may be folded one or more times before being placed in a wrapper. In some embodiments, the absorbent inserts may be folded twice before being placed in the wrapper.

In some embodiments, the absorbent inserts of the present invention include a first sheet, a second sheet, an intake layer, and an absorbent core. In these embodiments, the absorbent core may be positioned between the first sheet and the second sheet. Additionally, the intake layer may be positioned between the first sheet and the absorbent core. In this configuration, the first sheet is designated the body side and the second sheet is designated as the garment side of the absorbent insert.

In various embodiments, the absorbent insert may be folded a first time such that a first portion of the body side is in facing relation with a second portion of the body side. In these embodiments, the absorbent insert may be folded a second time such that a third portion of the body side is in facing relation with a first portion of the garment side. In other embodiments, the absorbent insert may be folded a first time such that a first portion of the garment side is in facing relation with a second portion of the garment side. In these embodiments, the absorbent insert may be folded a second time such that a third portion of the garment side is in facing relation with a first portion of the body side.

In some embodiments, the first fold may be positioned such that the absorbent insert is effectively folded into equal halves. In some embodiments, the first fold and the second fold may be positioned such that the absorbent insert is effectively folded into approximately equal thirds.

In various embodiments, the folded absorbent inserts may be individually packaged in any suitable wrapper material. Conventionally, the wrapper consists of one or more layers of a thin sheet or film of thermoplastic material, such as polyethylene, which is folded around the absorbent article and then sealed by the use of heat and/or pressure, ultrasonics, or an adhesive to form a package or pouch. In various embodiments, the wrapper may include films made from poly(vinyl alcohol), polyvinyl acetate, ethylene vinyl alcohol, polyurethane, ethylene methyl acrylate, and ethylene methyl acrylic acid to make them breathable. In some embodiments, the wrapper material may also be a laminate of different materials, such as a film/nonwoven laminate. The package may have a sealed side or edge that is designed to be opened by breaking or tearing the material at or adjacent the seal in order to subsequently remove the absorbent insert. With some package designs, a flap is provided that folds over the pouch opening and may attach to the front of the pouch with adhesive applied between the pouch and flap, or with a piece of adhesive tape. The sides of the flap may be sealed with the sides of the pouch and may be separated prior to removing the absorbent article.

When introducing elements of the present disclosure or the preferred aspect(s) thereof, the articles "a," "an," and "the" are intended to mean that there are one or more of the elements. The terms "comprising," "including," and "having" are intended to be inclusive and mean that there can be additional elements other than the listed elements.

The disclosure has been described with reference to various specific and illustrative aspects and techniques. However, it should be understood that many variations and modifications can be made while remaining within the spirit and scope of the disclosure. Many alternatives, modifications and variations will be apparent to those skilled in the art in light of the foregoing description. Accordingly, this disclosure is intended to embrace all such alternatives, modifications, and variations that fall within the spirit and scope of the appended claims.

We claim:

1. A permanently closed containment pant comprising,
   an elastically extensible chassis defining a waist opening, a first leg opening, and a second leg opening, the waist opening comprising a front waist region joined with a back waist region, and
   a sling positioned within the chassis and being joined to the front waist region and the back waist region, wherein the sling comprises a fluid-impervious base sheet and a containment flap joined with the base sheet to create a fluid-impervious pouch, and wherein the sling is attached to the chassis in a crotch region with an attachment mechanism to secure the sling to the chassis, the attachment mechanism comprising a bonded attachment and an attachment elastic material at a middle portion of the sling to the chassis at the crotch region; the sling further comprises a first transition and a second transition that are elastically extensible in a longitudinal direction and in a transverse direction, wherein the fluid-impervious base sheet is a fabric laminated with polyurethane to define a first polyurethane surface and a first fabric surface and the containment flap is a fabric laminated with polyurethane to define a second polyurethane surface and a second fabric surface, wherein the first polyurethane surface is ultrasonically joined in facing relationship with the second polyurethane surface.

2. The permanently closed containment pant of claim 1 wherein the fluid-impervious pouch defines a pouch floor having a first end section, a second end section, and a central section extending between the first end section and the second end section, wherein the first end section defines a maximum width, the second end section defines a maximum width equal to the maximum width of the first end section, and the central section defines a maximum width that is less than 70% the maximum width of the first and second end sections.

3. The permanently closed containment pant of claim 1 wherein the attachment elastic material stretches across the width of the fluid-impervious pouch in a transverse direction.

4. The permanently closed containment pant of claim 1 wherein the attachment elastic material stretches along the fluid-impervious pouch in a longitudinal direction.

5. A permanently closed containment pant comprising,
a chassis comprising a waist elastic joined proximate to and encircling a waist opening and a pair of leg elastics joined proximate to and encircling a pair of leg openings, the waist opening defining a front waist region and a back waist region, and
a sling positioned within the chassis and being joined to the front waist region and the back waist region, wherein the sling comprises a fluid-impervious base sheet and a containment flap joined with the base sheet to create a fluid-impervious pouch, and
wherein the sling is attached to the chassis in a crotch region with an attachment mechanism to secure the sling to the chassis, the attachment mechanism comprising the pair of elastics extending from leg openings and attaching to the sling in a crotch region; the sling further comprises a first transition and a second transition that are elastically extensible in a longitudinal direction and in a transverse direction, wherein the fluid-impervious base sheet is a fabric laminated with polyurethane to define a first polyurethane surface and a first fabric surface and the containment flap is a fabric laminated with polyurethane to define a second polyurethane surface and a second fabric surface, wherein the first polyurethane surface is ultrasonically joined in facing relationship with the second polyurethane surface.

6. The permanently closed containment pant of claim 5 wherein the fluid-impervious pouch defines a pouch floor having a first end section, a second end section, and a central section extending between the first end section and the second end section, wherein the first end section defines a maximum width, the second end section defines a maximum width equal to the maximum width of the first end section, and the central section defines a maximum width that is less than 70% of the maximum width of the first and second end sections.

7. The permanently closed containment pant of claim 5 wherein the pair of elastics extending from the pair of leg openings and attaching to the sling in the crotch region extend from the leg opening on a first side of the pant to a lateral side edge of the sling on an opposite side of the pant.

8. The permanently closed containment pant of claim 5 wherein the pair of elastics extending from the leg openings and attaching to the sling in the crotch region overlap.

9. The permanently closed containment pant of claim 5 wherein the chassis is formed of a front component joined to a back component at a crotch seam, and wherein additional pairs of leg elastics extend from both the front component and the back component, the additional pairs of leg elastics attaching to the sling in the crotch region.

10. The permanently closed containment pant of claim 9 wherein the additional pairs of leg elastics extending from both the front component and back component extend from the leg opening on a side of the pant to a lateral side edge of the sling on an opposite side of the pant.

11. The permanently closed containment pant of claim 9 wherein one of the additional pairs of leg elastics extending from the front component and attaching to the sling in the crotch region overlap, and wherein the other additional pair of leg elastics extending from the back component and attaching to the sling in the crotch region overlap.

12. A permanently closed containment pant comprising,
a chassis comprising a waist elastic joined proximate to and encircling a waist opening and a pair of leg elastics joined proximate to and encircling a pair of leg openings, the waist opening defining a front waist region and a back waist region, and
a sling positioned within the chassis and being joined to the front waist region and the back waist region, wherein the sling comprises a fluid-impervious base sheet and a containment flap joined with the base sheet to create a fluid-impervious pouch; wherein the base sheet is a fabric laminated with polyurethane to define a first polyurethane surface and a first fabric surface and the containment flap is a fabric laminated with polyurethane to define a second fabric surface and a second polyurethane surface wherein the first polyurethane surface is ultrasonically joined in facing relationship with the second polyurethane surface; and
wherein the sling further comprises a first transition and a second transition that are elastically extensible in a longitudinal direction and in a transverse direction and wherein the first transition is a discrete piece of material joined between the pouch and the waist elastic in the front waist region and wherein the second transition is a discrete piece of material joined between the pouch and the waist elastic in the back waist region, and
wherein the sling is attached to the chassis with an attachment mechanism, the attachment mechanism comprising an attachment bond in the first transition or second transition adjacent to the fluid-impervious pouch.

13. The permanently closed containment pant of claim 12 wherein the fluid-impervious pouch defines a pouch floor having a first end section, a second end section, and a central section extending between the first end section and the second end section, wherein the first end section defines a maximum width, the second end section defines a maximum width equal to the maximum width of the first end section, and the central section defines a maximum width that is less than 70% of the maximum width of the first and second end sections.

14. The permanently closed containment pant of claim 12 wherein the attachment bond comprises a single attachment bond.

15. The permanently closed containment pant of claim 12 wherein the attachment bond comprises a first attachment bond and a second attachment bond adjacent side edges of the first transition or the second transition.

16. The permanently closed containment pant of claim 12 wherein the attachment bond comprises a first attachment bond and a second attachment bond adjacent side edges of both the first transition and the second transition.

* * * * *